United States Patent [19]

Behrend

[11] Patent Number: 4,634,377

[45] Date of Patent: Jan. 6, 1987

[54] DEVICE FOR ALIGNING ARTIFICIAL TEETH AND CROWNS

[76] Inventor: Donald A. Behrend, 147 Collins Street, Melbourne, Victoria, Australia, 3000

[21] Appl. No.: 517,629

[22] Filed: Jul. 27, 1983

[30] Foreign Application Priority Data

Jul. 27, 1982 [AU] Australia ............................ PF5068
Dec. 24, 1982 [AU] Australia ............................ PF7460

[51] Int. Cl.$^4$ ............................................ A61C 19/04
[52] U.S. Cl. ........................................ 433/73; 433/68
[58] Field of Search ..................... 433/73, 72, 69, 68

[56] References Cited

U.S. PATENT DOCUMENTS

| | | | |
|---|---|---|---|
| 833,204 | 10/1906 | Crawford | 433/72 |
| 1,662,670 | 3/1928 | Harter | 433/73 |
| 2,475,706 | 7/1949 | Jamieson | 433/72 |
| 2,794,253 | 6/1957 | Fitzsimmons | 433/73 |
| 3,049,804 | 8/1962 | Skinner | 433/72 |
| 3,224,096 | 12/1965 | Stuart | 433/73 |
| 4,084,319 | 4/1978 | Dragan | 433/73 |
| 4,261,696 | 4/1981 | Hobo | 433/73 |

FOREIGN PATENT DOCUMENTS 2343471 10/1977 France ............................... 433/73

*Primary Examiner*—John J. Wilson

*Attorney, Agent, or Firm*—Keil & Weinkauf

[57] ABSTRACT

A system useful for recording or providing information concerning the optimal esthetic position and angulation of the anterior teeth of a dental patient during restoration of teeth with crowns or the construction of dental prostheses, the system utilizes five principal components:

a multi purpose positioning face bow including curved side arms adjustably interconnected by a linakage device for suspension from the ears of a patient with the linkage device and an associated bracket positioned below mouth level, the bracket adapted to support either, an adjustable transparent screen in a substantially vertical plane and positioned relative to a patient's mouth to obtain a transferable prescription of the position and angulation of anterior teeth for use on an articulator in another place, or a bite fork jig providing support for a interchangeable and invertible bite fork and an adjustable nose pointer, or a camera positioning frame for mounting a camera in fixed and constant relationship with the patient's anterior reference point and mouth to provide a photographic record, and a photographic frame for holding said photographic record for use with an articulator holding a model of the patient's teeth reproducing in the articulator some of the facial environment of the teeth.

10 Claims, 12 Drawing Figures

DEVICE FOR ALIGNING ARTIFICIAL TEETH AND CROWNS

FIELD OF INVENTION

This invention relates to a device for recording information concerning the optimal esthetic position and angulation of the anterior teeth of a dental patient as an aid to the restoration of teeth with crowns or the construction of dental prostheses. More particularly the invention relates to a system of recording information concerning the horizontal and vertical planes, the centre line and lip lines and antero posterior position of a dental patient.

Such crowns or prostheses are fabricated in a dental laboratory on models of the patient's ridges or prepared teeth. These models are mounted on an articulator, usually with the aid of a face bow. Pantograph or check bite recordings may be used to set the controls of the articulator to duplicate the movements of the patient's jaw. This system provides the dental technician with much of the information he needs regarding chewing function, i.e. the functional parameters of the case. What is lacking is the detailed information on the correct alignment and placement of the teeth relative to the patient's face to produce an appearance harmonious with the patient's face, i.e. the esthetic parameters of the case.

In conventional apparatus of one type the face bow may take the form as disclosed in U.S. patent specification No. 4,261,696 whilst the articulator may be as disclosed in U.S. patent specification No. 3,590,487.

The problem faced by the technician in determining the correct angulation and position of the anterior teeth in the frontal plane, i.e., the correct horizontal and vertical planes, is a particularly common and difficult one. Due to an asymmetry of the head, the reference points used in mounting the models may be at different levels on right and left. In this situation, the models will be mounted in a tilted position on the articulator. Consequently, the horizontal and vertical planes of the articulator resting on the laboratory bench can be a very misleading guide to the correct horizontal and vertical planes of the patient's face. Furthermore, the patient's natural occlusal plane, as indicated by the remaining teeth, may also not represent the correct horizontal plane of the face, but may slope from one side to the other. In this situation, if the occlusal plane cannot be made ideal by the prosthetic reconstruction, it is still essential for good esthetics that each tooth be set vertically, and not at right angles to that plane; i.e. there should be a "stepping" effect up or down from one side to the other. It is thus extremely important for the technician to have an objective guide to the correct horizontal and vertical planes of the patient's face.

A guide to the correct placement of the centre line mesio-distally and to the correct position of the incisal edges antero-posteriorly is also required, especially when several anterior teeth are missing. As before, the landmarks available to the technician from the mounted models may give a very misleading guide to the correct centre line of the face.

The outline of the lips, especially when the patient smiles, are of importance in determining the most esthetic incisal line for the anterior teeth. It is well accepted that the incisal line of the maxillary anterior teeth should, ideally, follow the curvature of the lower lip line in smiling. Once again, however, the technician conventionally has no information on this feature of the patient from the mounted models and the prescription. It is a frequent experience for a dentist to receive from the laboratory a set of anterior crowns or a prosthesis which appears satisfactory on the articulator but quite unsuitable for the patient when inserted in the mouth.

Prior methods of recording said information as known to applicant are the use of verbal descriptions, markings on wax rims or keys constructed from a temporary appliance. However, such methods are considered to be inaccurate, often time-consuming, and difficult for the dental technician to utilize, especially in the critical final stages of fabrication of the case. Reference is made to these problems by workers in the field who have published papers in the Journal of Prosthetic Dentistry as follows:

1. Stade, E. H., Hanson, J. G., and Baker, C. L.: Esthetic Considerations in the Use of Face-bows. Journal of Prosthetic Dentistry 48: 253, 1982.
2. Granger, R. G.: Dynamic Esthetics in Porcelain-veneered Fixed Prostheses. Journal of Prosthetic Dentistry 32: 534, 1974.

OBJECTIVE OF INVENTION

It is an objective of the present invention to provide a device for recording and transmitting to the dental laboratory information on esthetic parameters.

It is a specific object of the invention to provide a method and means for recording and transmitting information on the horizontal and vertical planes of a patient's face, the optimal centre-line and antero- posterior position of the teeth and the lip lines in which the teeth will appear.

There is provided according to the present invention a device for recording or providing information concerning the optimal esthetic position and angulation of the anterior teeth of a dental patient during restoration of teeth with crowns or the construction of dental prostheses comprising a transparent adjustable screen adapted to be mounted in a substantially vertical plane and in a predetermined position relative to a patient's mouth, said screen being rotatably and laterally adjustable in said substantially vertical plane to obtain a prescription of the alignment and centre line of a patient's mouth and optionally an outline of the patient's lips in the smiling position, said screen being transferable without disturbance of said prescription to an articulator upon which fabrication of crowns or prosthesis can be performed having reference to said prescription of vertical alignment and centre line of a patient's mouth.

Conveniently the screen mounting may include devices to control lateral and rotational movement, and be calibrated with scales so that the settings may be recorded in numerical form. Optional accessory devices are provided for positioning a life-sized photograph of the patient's lips in correct relationship to the models on the articulator.

There is provided by the present invention a positioning face bow including a pair of substantially parallel side arms, a linkage device adjustably connecting said arms to one another said arms having ear pieces at their opposite ends for suspension from the ears of a patient, said arms being curved such that in use the linkage device is positioned below the level of the patient's mouth.

Conveniently the linkage device includes a bracket for supporting a bite fork jig, a screen or a camera positioning frame.

In a more specific form the linkage device is positioned in use below the chin of the patient when the face bow is adjusted to the correct reference plane of the patient. The linkage device provides for adjustment of the distance between said arms in a manner similar to that disclosed in U.S. Pat. No. 4,261,696, and includes a support means having a slot extending antero-posteriorly in a substantially horizontal plane to support said components.

There is also provided by the invention for use in association with the alignment device and/or camera positioning device as described in the preceding paragraphs, a positioning face bow including a bracket means for mounting said adjustable screen in a predetermined position relative to the mouth of the patient, whereby a datum from which said recording of alignment and centre line and antero-posterior position of the teeth is established to allow accurate translation or transfer of said recording to a dental articulator.

There is provided according to the present invention a method of placing the positioning face bow with attached screen on the patient's head in accordance with the same reference points as used for a regular face bow. In this manner, the screen can eventually be mounted on the articulator in the same relationship to the models as it held to the patient's mouth when the recording was made.

While the screen is held in front of the patient's mouth by means of the positioning face bow, a recording of the optimal centre line, vertical alignment and the lip lines is made by adjusting and/or marking the screen as desired.

This adjustment and/or marking constitutes part of the prescription to be transmitted to the dental laboratory for construction of the dental appliance.

There is also provided according to a more specific aspect of the present invention a method of recording the optimal centre line position and vertical alignment for the anterior (front) teeth relative to the mouth or lips of a patient, comprising marking an anterior reference point on the patient's face (for example on the front or side of the nose) in the same plane as the auditory meatuses (ear channels), mounting a positioning face bow with a transparent screen mounted thereon, marking and/or adjusting said screen to indicate the vertical alignment and centre line and optionally marking the outline of the patient's lips, said marking and/or adjustment being a prescription for that particular patient for use in construction of crowns and/or dental prostheses on a dental articulator.

The invention will be described in greater detail with reference to the accompanying drawings. There are many proprietary lines of articulators and face bows available to which the present invention can be adapted. For purposes of illustration the practical arrangement will refer to a Denar (Trade Mark) face bow and a Denar articulator.

DESCRIPTION OF THE PREFERRED EMBODIMENTS

The system consists of five principal items: (1) a multi-purpose facebow, (2) a bite fork jig, (3) an adjustable transparent screen with horizontal and vertical markings, hereinafter referred to as a graticule, (4) a camera positioning frame and (5) a photograph holder. Items 4 and 5 are designed to be used with a particular camera and, together with item 2, may be regarded as optional accessories to the essential items 1 and 3.

There are many proprietary articulator systems to which the present invention can be adapted. For purposes of illustration the practical arrangement will refer to the Denar (Trade Mark) articulator system. Where dimensions are given they are those which apply to the particular form of the invention adapted to the Denar articulator system.

Figure 2:
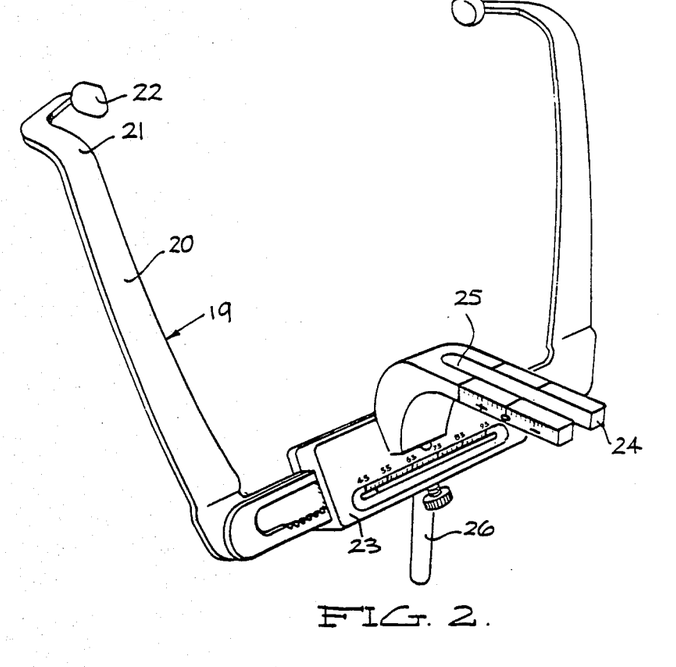
FIG. 2 is a perspective view of a face bow according to the invention.

MULTI-PURPOSE FACEBOW (FIG. 2)

Most existing facebows have arms and other mechanical parts which, in use, lie in front of the patient's face. For example refer to U.S. Pat. No. 4,261,696 previously referred to. This arrangement would be distracting if utilized when determining the optimal centre line and optimal vertical and horizontal planes of the patient's face. For this reason, the present face bow has arms 20 which are curved at 21 to bring the central portion of the facebow, the linkage device 23, below the patient's chin when the facebow is adjusted to the correct reference plane.

The linkage device has fixed to it a bracket 24 incorporating a track or slot 25 which runs antero-posteriorly in a horizontal plane. To this bracket may be fitted (1) the bite-fork jig see FIG. 6, or (2) the graticule see FIG. 1, or (3) the camera positioning frame see FIG. 7. A finger grip 26 is fixed centrally to the undersurface of the linkage device.

It is essential that all recordings on the patient be made in relationship to the same set of reference planes and points. In the case of the Denar Slidematic facebow; and the Denar articulator as disclosed in U.S. patent specification No. 3,590,487 the horizontal reference plane of the patient's head is defined by the two external auditory meatuses and a point 43 mm. above the incisal edges of the maxillary central incisors. The top surface of the lower member of the articulator is situated 95.25 mm. below the corresponding horizontal reference plane of the articulator. Hence, the maxillary model should be mounted with the incisal edges of the central incisors situated 52.25 mm. above the top surface of the lower member of the articulator.

The central section of the slotted bracket 24 defined by two transverse lines, corresponds in shape and dimensions to the slotted anterior end of the lower member of the Denar articular. (The bracket is, however, elongated anteriorly and posteriorly.) When the facebow is in correct position on the patient, the central section of the bracket occupies the same spacial relationship to the reference plane of the patient as the anterior end of the lower member of the articulator occupies to the reference plane of the articulator. Hence, a device such as the bite fork, the graticule or the camera frame mounted on the central section of the bracket of the facebow, when the facebow is correctly positioned, will bear the same relationship to the teeth as it will to the dental models when transferred to the articulator. In addition to the two transverse lines, the bracket is marked with a millimeter scale, the anterior transverse line coinciding with the zero mark. Graduations posterior to the zero mark are shown as "plus", those anterior to this mark as "minus".

The maxillary model can be mounted on the articulator by means of a Denar Slidematic facebow. If this is done, the reference point marked on the side of the nose should be supplemented or replaced by a reference point, line or adhesive marker on the front of the nose in the same plane. This will be required for positioning the graticule and/or the camera positioning frame to the same reference plane.

Alternatively, the multi-purpose facebow may be used to mount the maxillary model. For this purpose the bite fork jig is attached to the bracket.

Figure 6:
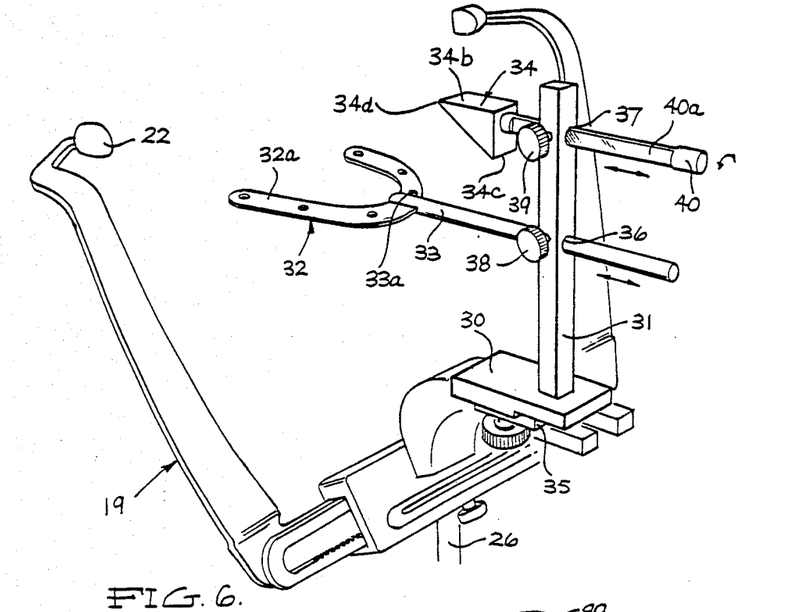
FIG. 6 is a perspective view of a bite fork jig mounted on a face bow in phantom outline.

BITE FORK JIG (FIG. 6)

The bite fork jig consists of a base block 30, a vertical rod 31 fixed to the base block, a bite fork 32 removably clamped to the vertical rod by stem 33 at a given level and a nose pointer/mounting support 34 removably clamped to the vertical rod at a higher level.

Figures 10, 11, 12:
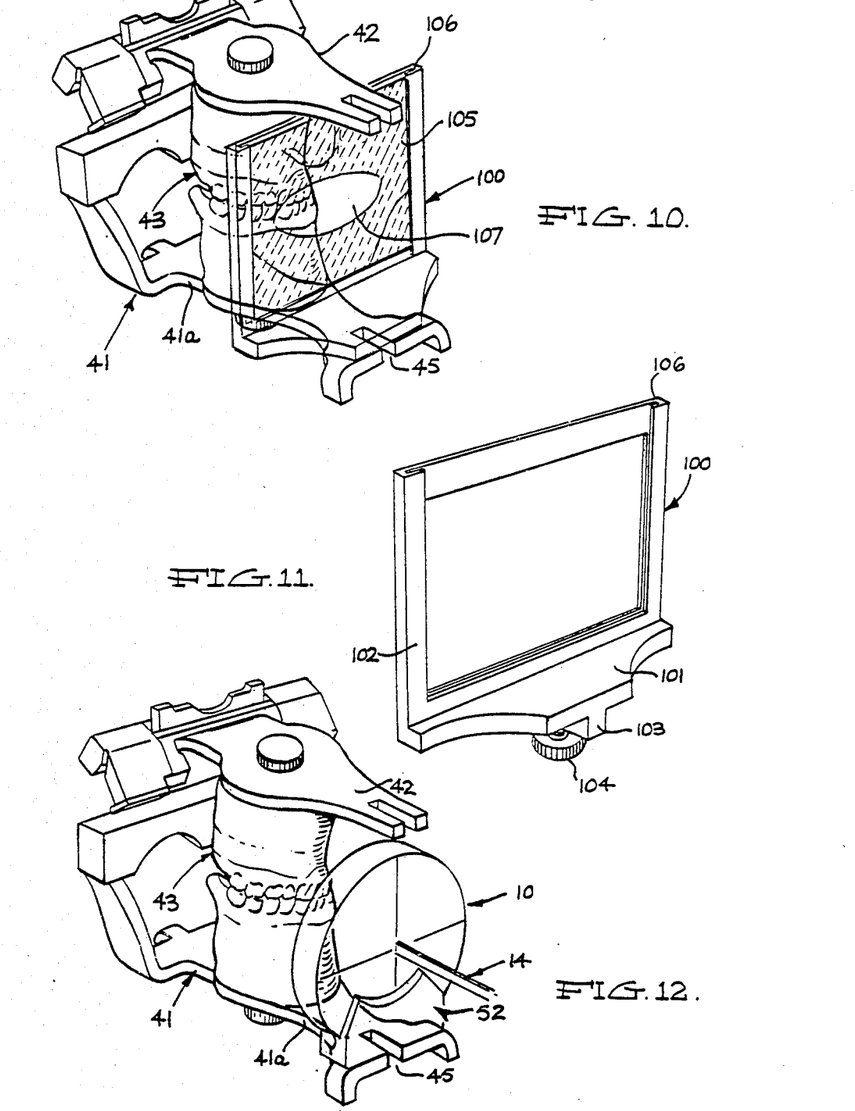
FIG. 10 is a frontal perspective view of a dental model on an articulator with a photograph frame superimposed in phantom.
FIG. 11 is a perspective view of a photograph frame.
FIG. 12 is a perspective view of a dental model on an articulator with the transparent screen superimposed in phantom.

The base block 30 has on the posterior part of its under-surface a rectangular key 35 to fit the slotted bracket 24 of the facebow 19 (FIG. 2) and the slotted end 45 of the lower member of the articulator 41 (FIG. 10). A screw clamp on the under-surface of the key secures the base block 30 in position on the facebow or articulator.

The vertical rod extends upwards from the anterior part of the base block. The rod is apertured antero-posteriorly by two holes 36,37 at given levels for mounting of the bite fork 32 and nose pointer/mounting support 34.

The bite fork 32 consists of a stem 33 and a U-shaped perforated plate 32a rigidly joined. The stem is round in section to fit the lower hole 36 in the rod, in which it is fixed by a set screw 38. The stem extends across the anterior part of the plate 32a with its upper surface 33a short distance above the upper surface of the plate. The upper surface of the stem 33a is intended to contact, or to occupy to position of, the incisal edges of the maxillary central incisors. Hence, it is fixed at a level 52.25 mm. above the under-surface of the base block 30 (excluding the key). This height will not be altered by rotation of the bite fork 32 to accommodate an occlusal plane which is tilted from right to left. A bite fork with horizontal perforated plate (as shown) may be used for most cases. One or more alternative bite forks with the perforated plate tilted upwards (or, when reversed, downwards) may be supplied for use when the patient's occlusal plane is markedly tilted antero-posteriorly.

The nose pointer/mounting support 34 consists of a stem 40 and a wedge-shaped block 34a rigidly joined. The stem 40 is generally round-sectioned but reduced on two sides to give opposed flat surfaces 40(a). The stem 40 passing through the upper hole 37 in the vertical rod, is fixed by a set screw 39 bearing against either of the flat surfaces. With the horizontal surface 34b of the wedge-shaped block 34a uppermost, its posterior edge 34d acts as a pointer to establish, and to be aligned with, the reference mark on the front of the patient's nose. Its height above the under-surface of the base block is therefore fixed at 95.25 mm. When the stem is rotated through 180°, the upper anterior edge 34c of the wedge-shaped block lies at the correct level to support the upper member 42 of the articulator 41 during mounting of the maxillary model 43.

In use, the jig is mounted on the facebow 19 with the posterior portion of its base block 30 in the central section of the bracket 24, i.e. between the two transverse lines. The facebow is fitted to the patient with the earplugs 22 firmly inserted in the external auditory meatuses and a suitable bite fork, adjusted to the patient's maxillary arch, inserted in the mouth. Maintaining gentle anterior traction on the finger grip 26, the facebow is pivoted upwards around the ear plugs until the stem of the bite fork contacts the incisal edges of the maxillary central incisors or lies at the level which they should occupy. A piece of wax attached to the front of the bite fork may be used to steady the fork at this level when the maxillary incisors have been prepared for crowns or are missing. For an edentulous patient, a baseplate with bite rim should be in place. The nose pointer 34 is now extended to contact the nose and the reference mark (e.g. a small circular adhesive label) is placed on the front of the nose at this level. Thus, the facebow with bite fork jig provides a most accurate and convenient method for locating the anterior reference point.

The nose pointer 34 is retracted and the facebow 19 pivoted down. A mix of soft registration material, such as a polyether paste, is injected between the maxillary teeth and the bite fork 32. The facebow is now pivoted upwards to its original position, again maintaining gentle anterior traction on the finger grip. The nose pointer 34 is moved posteriorly to contact the nose and confirm the correct positioning of the facebow. The face bow is held steady until the registration material sets, and is then removed from the patient and checked for a clear impression of the teeth.

The bite fork jig is taken off the face bow and sent to the laboratory for mounting of the maxillary model 43. For this procedure, the nose pointer 34 is rotated through 180° so that it may act as a mounting support for the upper member 42 of the articulator 41 (from which the incisal guide pin has been removed).

In most conventional systems a bite fork is held in the mouth and is then secured to a facebow by tightening screws on a universal clamp. This procedure of tightening tends to twist the facebow and alter its relationship to the bite fork. The present invention, by having the bite fork 32 fixed to the facebow 19 in advance and recording the position of the teeth under passive conditions, avoids this source of error.

GRATICULE (FIGS. 1, 3, 4 and 5)

Figure 1:
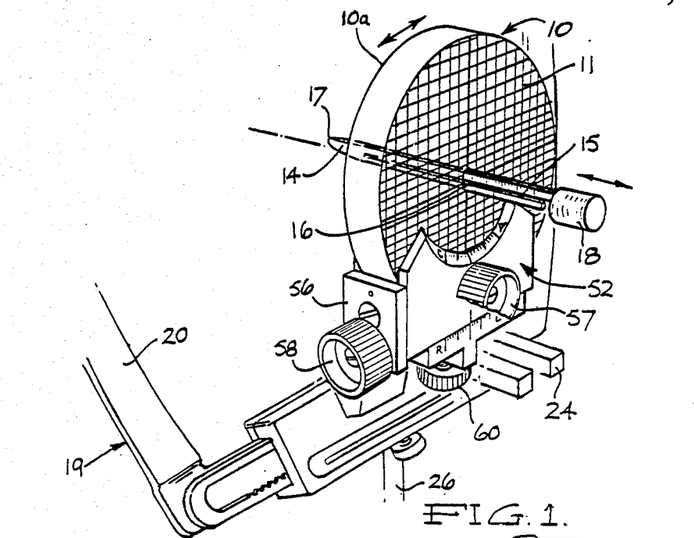
FIG. 1 is a perspective view of an adjustably mounted transparent screen with a face bow shown in phantom outline.

The graticule 10 consists of a transparent circular screen 10a, transfixed by a pointer 14, and supported by a mounting block 52. The mounting block has a means for (1) rotating the screen 10a around its centre clockwise or anticlockwise and (2) moving the screen 10a bodily to right or left.

The screen 10a is constructed of a transparent material such as clear acrylic and is inscribed on its anterior surface with a grid of straight lines 11 at right angles to one another. The central vertical and central horizontal lines are marked more heavily than the other lines. The vertical lines are spaced approximately 5 mm. apart. At this spacing, with most patients, when the central vertical line coincides with the centre line of the dentition the first three vertical lines from the centre on each side will lie over the maxillary central incisor, lateral incisor and cuspid respectively.

Figure 3:
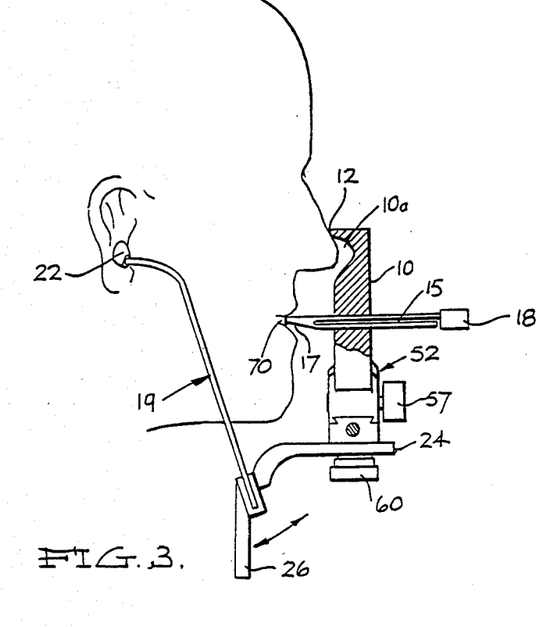
FIG. 3 is a side elevation showing an application of the transparent screen and face bow.

The posterior surface of the screen 10a may be shaped so that its upper border forms a rim 12 see FIG. 3 projecting posteriorly which can be aligned with the reference mark on the front of the nose, while the tip of the nose lies beneath the rim. The radius of the screen 10a is 43 mm., so that when the highest point of the rim 12 is in contact with the reference mark on the nose the centre of the screen 10a is level with the incisal edges of the maxillary central incisors 70.

A pointer 14, adjustable antero-posteriorly, passes perpendicularly through the centre of the screen. It is rectangular in section with a longitudinal slit 15 to give a frictional fit in the rectangular hole 16 passing through the screen. Its posterior end is tapered from below and each side to terminate in a screwdriver-shaped tip 17, the lower corner of which is in line with the central axis of the screen. The anterior end has a knob 18 attached only to the upper half. One side of the pointer is marked along its length with a millimeter scale which, when read against the anterior surface of the screen, indicates the extension of the pointer beyond the posterior surface of the screen.

The lower part of the screen (see FIGS. 4 and 5) is perforated by a curved slot 50, concentric with the periphery of the screen, and having a toothed lower surface 51 to form a curved rack.

The mounting block 52 consists of a base piece 54, an anterior piece 53, a posterior piece 55, a side piece 56 and several small parts such as screws and knobs 57 and 58.

The base piece 54 has a rectangular key 59 to fit the bracket 24 of the face bow 19 and the lower slot 45 of the articulator 41 and a screw clamp 60 to secure it in position on either of these.

The upper surface of the base piece 54 and the lower surface of the pieces 53 and 55 are held together by a dovetail-sectioned track 61 allowing the upper portion of the mounting block 52 to slide right and left on the base piece 54. The extent of this displacement is indicated by the movement of a mark on the anterior piece across a graduated scale 62 on the base piece 54. The displacement is shown in millimeters right (R) or left (L) of centre. The movement is controlled by a screw 56a passing through the side piece 56 (which is fixed to the anterior piece 53 and acts as a thrust plate), engaging a thread in the base piece 54. The end of the screw carries a knurled knob 58.

The anterior piece 53, which is approximately L-shaped in section, forms together with the posterior piece 55, a housing for the lower part of the screen 10. This housing has a curved floor to match the curvature of the lower edge of the screen, which can therefore rotate within the housing around its own centre.

Figures 4, 5:
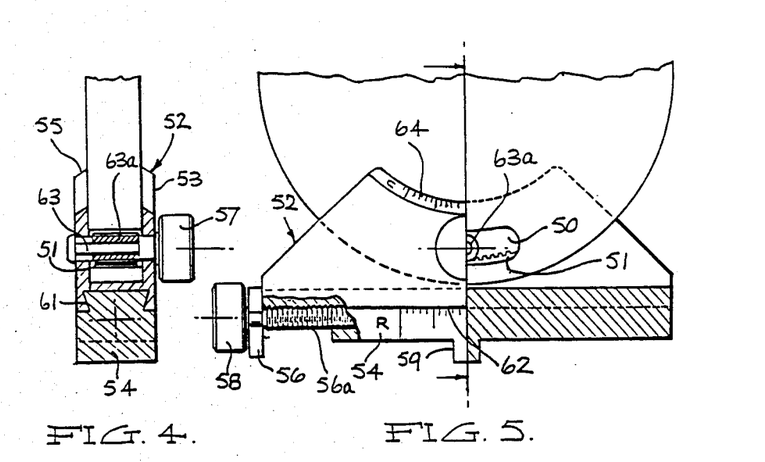
FIGS. 4 and 5 are partial elevational sectional views of the transparent screen.

The screen 10a is held against the curved base of the housing by a spindle 63 covered with a sleeve of rubber 63a passing through the curved slot 50. The rubber sleeve is held between two cups which can be drawn closer together by tightening of a nut. This compresses the rubber lengthwise, causing it to bulge laterally and engage the toothed rack 51 which forms the lower border of the curved slot 50.

The extent of the rotation of the screen 10a from the central position is indicated by the movement of its vertical centre line around an angular graduated scale 64 on the upper part of the anterior piece 53. The units of the scale are 2 degrees each, extending clockwise (C) or anticlockwise (A) from the centre. The movement is controlled by a knurled knob 57 at the end of the spindle 63.

The overall height of the graticule, from the undersurface of the base piece 54 (excluding the key) to the top of the screen 10a, is 95.25 mm.—i.e. the height from the lower member 41a of the articulator 41 (FIG. 12) to the reference plane.

In use, the graticule 10 is mounted on the facebow 19 with the key 59 at the anterior end of the slotted bracket 24. The pointer 14 is retracted. The facebow is fitted to the patient as previously described and the graticule 10 is moved posteriorly along the bracket 24 until the rim 12 at the top of the screen contacts the nose (see FIG. 3), the facebow being pivoted upwards or downwards to make the upper edge of the rim coincident with the reference mark on the nose. The screw clamp securing the graticule to the bracket is tightened. The pointer 14 is advanced until its tip 17 is close to the incisal edges of the maxillary central incisors 70, or their supposed position.

With the facebow held in position by gentle anterior traction on the finger grip 26, the lateral and rotary positions of the screen 10 are adjusted by means of the two knurled knobs 57,58. The pointer 14 is used to indicate the position of the centre line, and the horizontal and vertical lines on the screen the ideal alignment for the teeth. In choosing the best settings the dentist should take into consideration the patient's whole face, including the line of the eyes, the nose, the outline of the lips and the occlusal plane of any remaining teeth. The chosen line will often represent a compromise between the varying demands of these features. The extension of the pointer 14 is adjusted to indicate the correct antero-posterior position for the incisal edges of the maxillary incisors 70.

The various settings are noted either before or after removal of the face bow and graticule from the patient. The lateral setting of the screen is recorded in millimeters R or L and the rotary setting in "units" (each representing 2 degrees) C or A. The antero-posterior position of the graticule along the bracket is recorded in millimeters "plus" or "minus" and this figure is added to, or subtracted from, the figure shown on the scale along the pointer. The composite figure will indicate the desired extension of the pointer to the incisal edges when the graticule is centrally placed on the bracket (or fitted to the lower bow of the articulator).

Ideally, another graticule 10 will be kept at the laboratory; otherwise the dentist's graticule is sent with the prescription. In the laboratory, the graticule is set in accordance with the prescription. By removing the incisal guide pin and the incisal guide table from the articulator, the technician may mount the graticule on the articulator 41 as shown in FIG. 12 to establish or check the position and angulation of the artificial teeth or crowns.

In complete denture construction dentists conventionally use a wax rim to indicate to the technician the desired position of the maxillary incisors. Even if a technician receives only this information he will still find it advantageous to mount his graticule on the articulator and set it according to the wax rim. He can then keep a record of the esthetic parameters in permanent numerical form and can use the set graticule to monitor the position of the artificial teeth at each stage of the denture construction. Otherwise the records are lost early in the process with the destruction of the wax rim.

Figure 7:
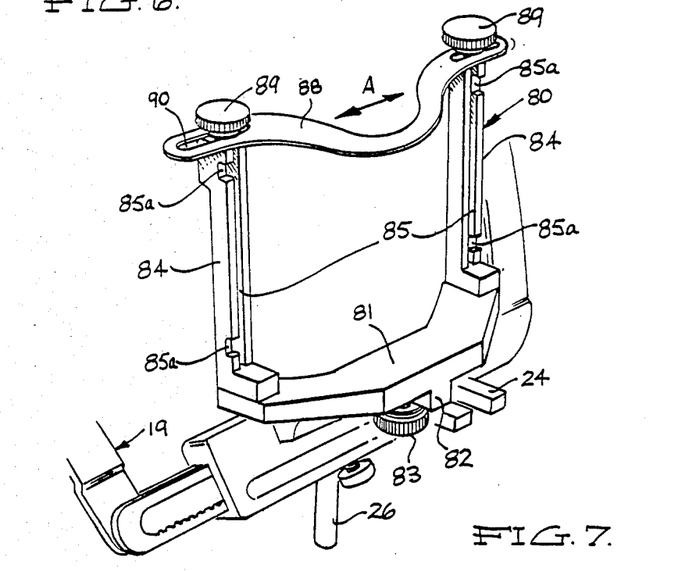
FIG. 7 is a perspective view of a camera positioning frame.
Figure 8:
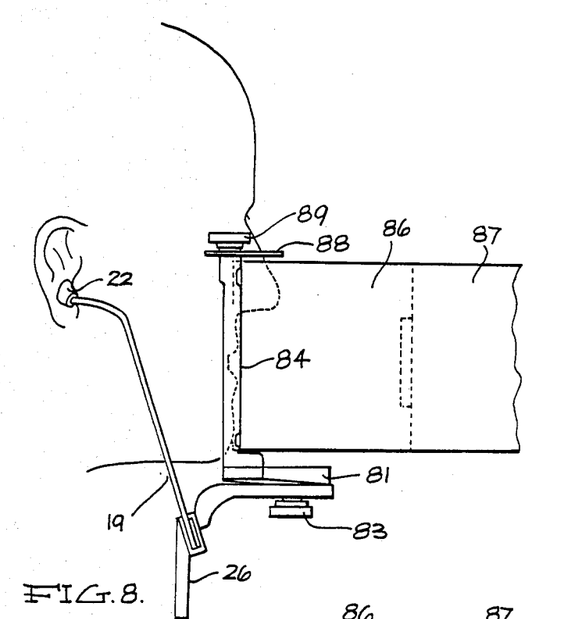
FIG. 8 shows an elevational view of the camera positioning frame, camera and face bow.
Figure 9:
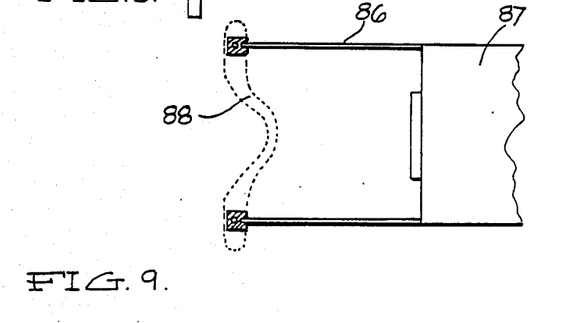
FIG. 9 is a diagrammatic plan view of camera frame and camera.

CAMERA POSITIONING FRAME (FIGS. 7, 8 and 9)

The camera positioning frame 80 is designed to be used with the Polaroid CU5 (Trade Mark) camera fitted with a 3-inch lens and a 1:1 frame.

The camera positioning frame 80, viewed from the front, consists of an open rectangle. The base piece 81 is approximately U-shaped to accommodate the patient's chin and has a rectangular key 82 and a screw clamp 83 on its under-surface to enable it to be fitted to the bracket 24 of the facebow 19. The two side pieces 84 are rigidly attached to the base piece 81 and each has a vertical groove 85 on its anterior surface. The length, width and spacing of these two grooves are such as to receive the "wings" 86 of the 1:1 frame of the Polaroid CU5 camera 87. A small section 85a cut away from the outer wall of each groove 85 at top and bottom enables the correct seating of the wings 86 within the grooves to be observed. The top piece of the frame, hereinafter known as the nose piece 88, is a flat piece of material shaped to accommodate the nose at the level of the reference mark. The nose piece 88 is held on the top of the side pieces by screw clamps 89 passing through elongated slots 90. Thus, the nose piece can be moved some distance to right or left, arrow A, according to the position of the nose.

The height from the under-surface of the base piece 81 (excluding the key 82) to the top surface of the nose piece is 95.25 mm., i.e. the height from the lower member 41a of the articulator to the reference plane.

In use, the camera positioning frame is mounted on the bracket 24 of the facebow and fitted to the patient as before, with the top surface of the nose piece 88 coincident with the reference mark on the front of the nose FIG. 8. The two screw clamps 89 are loose during fitting to allow the nose piece 88 to adjust its position laterally to the nose. The screw clamp 83 of the base piece 81 and the screw clamps 89 of the nose piece are then tightened.

The camera is brought up and the two wings 86 of the 1:1 frame are introduced into the grooves 85. The facebow 19 must be held steady to prevent displacement during this procedure. The full seating of the 1:1 frame into the grooves 85 is verified by viewing through the openings 85a at top and bottom of each groove. With the patient smiling, the release trigger (not shown) of the camera 87 is pressed to take the photograph. Additional photographs for record purposes, e.g. with a self-retaining lip-retractor in place, may be taken in this standardized position. The photographs can be developed in one minute and checked.

The vertical position of the grooves 85 in relation to the nose piece 88 is such that, when the photograph is developed, the upper edge of the print corresponds in position to the top surface of the nose piece 88.

Serial, standardized record photographs taken in this way may be useful in many branches of dentistry, including orthodontics.

As an aid in the construction of anterior crowns and prostheses, a photograph taken as above with the patient smiling is included with the prescription. In the laboratory, it is utilized by means of the photograph holder.

PHOTOGRAPH HOLDER (FIGS. 10, 11)

The photograph holder 100 consists of a base piece 101 supporting a rectangular frame 102.

The base piece 101 has a rectangular key 103 and screw clamp 104 on its undersurface to enable it to be fitted to the lower member 41a of the articulator 41 in slot 45. The position of the key is such that, when mounted on the articulator, the screen is close to the models 43. The key 103 is made shorter than the slot 45 in the lower member of the articulator to allow for some antero-posterior adjustment of the photograph holder.

The frame 102 has side pieces and a bottom piece with slots 106 to retain the photograph 105, which is inserted from above. When fully inserted, the upper edge of the photograph is level with the upper surface of the top piece of the frame 102.

The height from the under-surface of the base piece (excluding the key) to the upper edge of the frame is, again, 95.25 mm. corresponding to the height of the reference plane above the lower member of the articulator. Thus, with the photograph inserted and the photograph holder mounted on the articulator, the image on the photograph, viewed from the front, will occupy the same relationship to the model 43 as it did to the patient's teeth.

The photograph 105 is prepared for use in the laboratory by cutting around the inner outline of the lips with a pair of fine, curved scissors. This leaves an opening 107 through which the teeth would normally appear. The prepared photograph is inserted in the photograph holder 100 and the latter may then be mounted on the articulator in the same way as the graticule see FIG. 10. Like the graticule, it may be used by the technician as a guide to the construction of the crowns or prosthesis at any stage.

The use of a photograph in this way reproduces on the laboratory bench some of the facial environment of the teeth. In particular, it guides the technician in developing an incisal line for the maxillary anterior teeth which follows the curvature of the lower lip in smiling. Used in conjunction with the graticule, it gives the technician a greatly improved opportunity of producing a result harmonious with the patient's face.

The present system as described utilizes the external auditory meatuses as the posterior reference locations. If it is desired to use the extensions of the hinge axis of the patient as the posterior reference points, it will be necessary to use an additional device and a modified form of the face bow.

An adjustable head cap or band would hold right and left flags over the condyle areas. The flags would be of clear plastic with a matrix of closely-spaced perforations.

The facebow would have a short needle at the end of each arm, situated 13 mm. anterior to the position of the present ear plugs. The facebow would be constructed so that either the ear plugs or the needles could be fitted to the arms.

In use, the right and left hinge axis extensions would be located by conventional means and the needles of the facebow would be inserted into the perforations in the flags nearest to these points. The rest of the procedure would be as described previously.

For greater convenience in the laboratory, the technician's graticule and the photograph holder can each be made to hinge from the top or the side so that they may be swung out of the way while working on the models. Further, a mounting can be designed so that both graticule and photograph holder are mounted at once, one hinged to the right and the other to the left, so that either could be swung into position as required.

I claim:

1. A device for recording or providing information concerning the anulation of the anterior teeth of a dental patient during restoration of teeth with crowns or the construction of dental prostheses, including a transparent screen mounted on a support means for positioning said screen in a substantially vertical frontal plane and in a predetermined position in front of the patient's mouth, said screen having horizontal and vertical lines marked thereon, said support means comprising a calibrated support block, said screen being rotatably adjustable on said calibrated support block to obtain a prescription of the angulation of said anterior teeth, said prescription being transferable to an identical screen mounted on an articulator upon which fabrication of said crowns and prostheses can be performed having reference to said prescription.

2. A device for recording or providing information concerning the optimal esthetic position and angulation of the anterior teeth of a dental patient during restoration of teeth with crowns or the construction of dental prostheses, including a transparent screen adapted to be mounted in a substantially vertical frontal plane and in a predetermined position in front of the patient's mouth, said screen having spaced vertical and horizontal lines marked thereon, said transparent screen being mounted on a support block including means to control lateral and rotational movement of the screen, said support block including calibrations to enable recording of said screen movement, said screen being rotatably and laterally adjustable in said frontal plane to obtain a prescription of the position and angulation of said anterior teeth, said prescription being transferable to an identical said transparent screen mounted on an articulator upon which fabrication of said crowns and prostheses can be performed having reference to said prescription.

3. A device as claimed in claim 2 wherein said screen includes a graduated pointer extending through said screen adapted to locate and record the central point of the patient's maxillary anterior teeth and the antero-posterior position of their incisal edges.

4. A device as claimed in claim 2, including a positioning face bow including a pair of substantially parallel side arms, a cross-member connecting said arms to one another, said arms having ear pieces at their opposite ends for suspension from the ears or hinge axis points of a patient, wherein said arms are directed downwardly such that in use the cross-member is positioned below the level of the patient's mouth, said cross-member adapted to hold said support block, the arrangement being such that in use the arms and cross-member do not interfere with or obscure a frontal view of the patient's face.

5. A method of recording the optimal esthetic position and angulation of the anterior teeth of a patient, comprising the steps of: marking an anterior reference point on the patient's face in the same plane as the auditory meatuses or hinge axis points, mounting a positioning face bow with a transparent screen mounted thereon in a substantially vertical plane and in a predetermined position in front of the patient's mouth, marking said screen to indicate the vertical alignment and centre line and optionally marking the outline of the patient's lips, said marking being a prescription for that particular patient, transferring said screen without disturbance of said markings to an articulator for use in construction of crowns and dental prostheses on the articulator.

6. The method of claim 5, wherein said transparent screen has spaced vertical and horizontal lines marked thereon, and including the steps of locating the screen in a substantially vertical frontal plane and a predetermined position in front of the patient's mouth, adjusting the screen laterally and rotatably in said frontal plane relative to said mounting, taking a reading of the relative position of said screen by the calibrations on a support block and applying said reading to an identical screen mounted on an articulator for use in the construction of crowns and dental prostheses on the articulator.

7. A method as claimed in claim 6 wherein said screen includes a graduated pointer extending therethrough comprising the step of positioning the pointer to locate and record the central point of the patient's maxillary anterior teeth and the antero-posterior position of their incisal edges.

8. A method of claimed in claim 5 wherein said transparent screen has spaced vertical and horizontal lines marked thereon and including the steps of locating the screen in a substantially vertical frontal plane and a predetermined position in front of the patient's mouth, adjusting the screen laterally and rotatably in said frontal plane relative to said mounting to obtain a prescription, and transferring said screen and prescription without disturbance to said articulator.

9. A method of recording information concerning the angulation of the anterior teeth of a dental patient during restoration of teeth with crowns or the construction of dental prostheses, comprising the steps of: marking an anterior reference point on the patient's face in the same plane as the auditory meatuses or hinge axis points, mounting a positioning face bow with a transparent screen mounted thereon in a substantially vertical plane and in a predetermined position in front of the patient's mouth, said screen having spaced vertical and horizontal lines marked thereon, rotatably adjusting said screen in said frontal plane relative to said mounting to obtain a prescription of the angulation of said anterior teeth, transferring said prescription to an articulator, fabricating said crowns and prostheses on the articulator having reference to said prescription.

10. A method for recording or providing information concerning the optimal esthetic position and angulation of the anterior teeth of a dental patient during restoration of teeth using a positioning face bow including a pair of substantially parallel side arms, a cross-member connecting said arms to one another, said arms having ear pieces at their opposite ends, including the steps of:

suspending said face bow from the ears of a patient such that in use said cross-member is positioned below the level of the patient's mouth so as not to obscure the mouth and face, securing a camera positioning frame on said cross-member adjacent to the mouth and face, positioning a camera in the frame to enable a photographic record of the lips of a patient to be made, preparing the photograph by cutting out the part representing the open mouth, positioning the photograph in a photograph frame on an articulator holding a model of the patient's teeth, said frame adapted to be mounted on said articulator to support said photograph in fixed and constant relationship to said model, to show the position of the patient's face and lips in close proximity to the model of the patient's teeth on the articulator.

* * * * *

UNITED STATES PATENT AND TRADEMARK OFFICE
CERTIFICATE OF CORRECTION

PATENT NO. : 4,634,377

DATED : January 6, 1987

INVENTOR(S) : Behrend

It is certified that error appears in the above-identified patent and that said Letters Patent is hereby corrected as shown below:

In The Abstract:

[linakage] should be linkage.

In the Claims:

Column 11, line 21: [anulation] should be angulation

Signed and Sealed this

Thirty-first Day of March, 1987

Attest:

DONALD J. QUIGG

Attesting Officer

Commissioner of Patents and Trademarks